United States Patent [19]
Frenkel

[11] Patent Number: 5,230,997
[45] Date of Patent: Jul. 27, 1993

[54] METHODS OF DETECTING THE PRESENCE OF HUMAN HERPESVIRUS-7 INFECTION

[75] Inventor: Niza Frenkel, Rockville, Md.

[73] Assignee: The United States of America as represented by the Department of Health and Human Services, Washington, D.C.

[21] Appl. No.: 553,798

[22] Filed: Jul. 19, 1990

[51] Int. Cl.$^5$ ............... C12Q 1/70; G01N 33/571
[52] U.S. Cl. ............... 435/5; 435/235.1; 435/7.1; 435/7.5; 435/810; 436/511; 530/389.4; 530/388.3
[58] Field of Search ............... 435/5, 6, 7.1, 7.5, 435/91, 172.3, 252.3, 320.1, 69.1, 240.21, 235.1, 810; 530/387; 436/511; 536/27; 935/6

[56] References Cited

PUBLICATIONS

Lawrence et al., Journal of Virology, vol. 64, No. 1, Jan. 1990, pp. 287-299.

*Primary Examiner*—Robert J. Hill, Jr.
*Assistant Examiner*—Laurie Scheiner
*Attorney, Agent, or Firm*—Knobbe Martens Olson & Bear

[57] ABSTRACT

The present invention relates to a new human herpesvirus-7, proteins encoded in the genome of the virus, and antibodies specific for the virus and proteins. The virus was isolated from human peripheral blood mononuclear cells following incubation of the cells under conditions promoting T cell activation. Cultures of lymphocytes infected with the virus exhibited a cytopathic effect and electron microscopic analyses revealed a characteristic herpesvirus structure. The new virus is distinct from previously characterized human herpesviruses.

The invention also relates to bioassays for the diagnosis of human herpesvirus-7 and the detection of human herpesvirus-7 in a biological sample. It further relates to a vaccine for humans against human herpesvirus-7.

26 Claims, 9 Drawing Sheets

FIG.1f
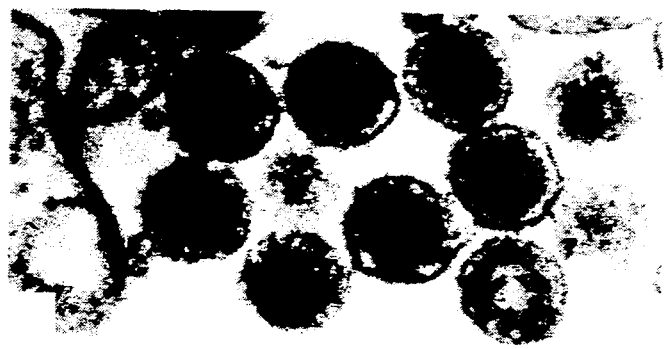
FIG.1e
FIG.1a
FIG.1d
FIG.1c
FIG.1b

METHODS OF DETECTING THE PRESENCE OF HUMAN HERPESVIRUS-7 INFECTION

BACKGROUND OF THE INVENTION

1. Field of the Invention

The present invention relates in general to herpesviruses and in particular, to human herpesvirus-7. The present invention also relates to methods of detection and diagnosis of the presence of the human herpesvirus-7.

2. Background Information

Herpesviruses are large DNA-containing viruses which share architectural features of their virion, including a DNA core, an icosadeltahedral capsid with 162 capsomers, an amorphous tegument, and an envelope (Roizman, B. (1982) in The herpesviruses. Vol. 1. ed. Roizman, B. (Plenum York), pp. 1-23.) Members of the Herpesviridae family have been isolated from more than 80 different animal species. Six different herpesviruses of man have thus far been described. The most recent one to be identified (Salahuddin, S. Z., Ablashi, D. V., Markham, P. D., Josephs, S. F., Sturzenegger, S., Kaplan, M., Halligan, G., Biberfeld, P., Wong-Staal, F., Kramarsky, B., and Gallo, R. C. (1986) Science 234, 596–601.), human herpesvirus 6 (HHV-6), is the causative agent of roseola infantum, a common childhood disease characterized by high fever and skin rash (Yamanishi, K., Okuno, T., Shiraki, K., Takahashi, M., Kondo, T., Asano, Y., and Kurata, T. (1988) Lancet i, 1065–1067.). HHV-6 exhibits predominant T cell tropism (Agut, H., Guetard, D., Collandre, H., Dauguet, C., Montagnier, L., Miclea, J. M., Baurmann, H., Gessain, A. (1988) Lancet i, 712., H., Dauguet, C., Montagnier, L., Miclea, J. M., Baurmann, H., Gessain, A. (1988) Lancet i, 712., Downing, R. G., Sewankambo, N., Serwadda, D., Honess, R., Crawford, D., Jarrett, R., Griffin, B. E. (1987) Lancet ii, 390., Lopez, C., Pellett, P., Stewart, J., Goldsmith, C., Sanderlin, K., Black, J., Warfield, D., Feorino, P. (1988) J Infect Dis 157, 1271–73., Lusso, P., Markham, P. D., Tschachler, E., Veronese, F. dM., Salahuddin, S. Z., Ablashi, D. V., Pahwa, S., Krohn, K., Gallo, R. C. (1988) J Exp Med 167, 1659–1670., Takahashi, K., Sonoda, S., Higashi, K., Kondo, T., Takahashi, H., Takahashi, M., Yamanishi, K. (1989) J. Virol. 63, 3161–3163).

In the course of a study of human immunodeficiency virus (HIV-1) in the laboratory of Dr. Carl H. June at the Naval Medical Research Institute, it was noted that a culture of uninfected activated CD4+ cells obtained from a healthy individual (RK) exhibited spontaneous cytopathic effect (CPE). The cells were negative for HIV-1 as judged by reverse transcriptase activity and absence of p24 antigen by antigen capture assay. The cultures were transferred to the National Institute of Allergy and Infectious Diseases/Twinbrook, where a herpesvirus with distinct properties was isolated and characterized. One of the salient features of the present invention was to isolate and propagate the virus and expose it to tests which led to its identification as a new human herpesvirus.

SUMMARY OF THE INVENTION

Accordingly, it is an object of the present invention to provide a new herpesvirus, designated human herpesvirus 7 (HHV-7).

It is another object of the present invention to provide diagnostic tests specific for the human herpesvirus 7.

Various other objects and advantages will be apparent from the drawings and the following description of the invention.

BRIEF DESCRIPTION OF THE DRAWINGS

FIG. 1 shows virion structure and CPE exhibited by HHV-7 (prototype strain RK). Specifically, FIGS. 1a, 1b, 1c and 1d show cells viewed in the light microscope set at 200 fold magnification; 1a, Mock infected cells; 1b, 1c and 1d, HHV-7 (RK) infected cells (7 days post infection) showing refractile ballooning cells with distinct binding membrane and cells which appear to undergo fusion. FIGS. 1e and 1f show virions viewed in the electron microscope.

DETAILED DESCRIPTION OF THE INVENTION

Figure 2:
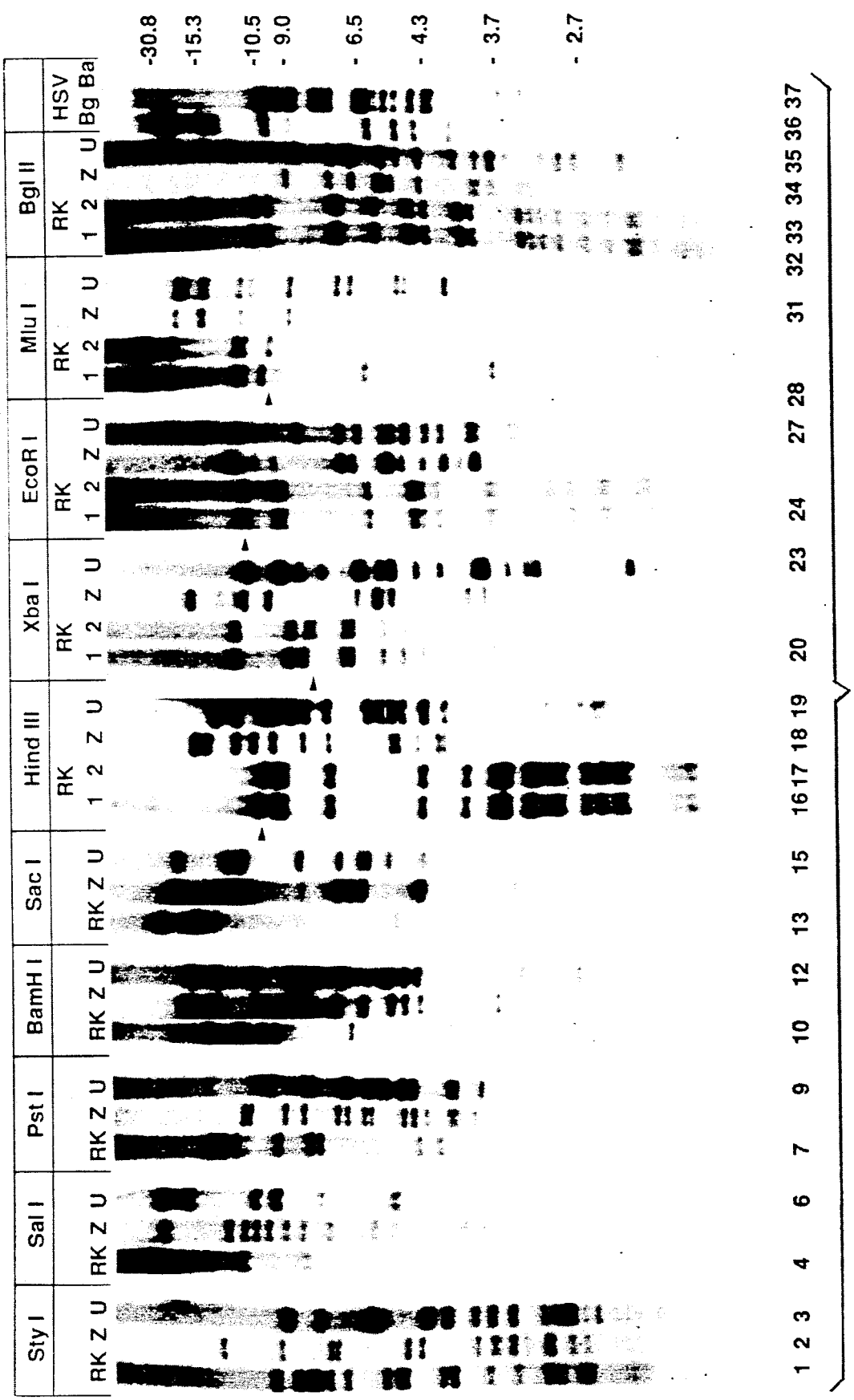
FIG. 2 shows restriction enzyme patterns. $^{32}$P-labeled DNA was prepared from PBL cultures infected with the HHV-6 strains U1102 (U) or Z29 (Z), or with two isolates of HHV-7 (RK) (R 1 and 2). Cleavage of DNA from isolates 1 and 2 with HindIII, XbaI, EcoRI and MluI produced similar patterns except the variant bands marked with arrows. Lanes 36 and 37 contain mw markers consisting of BglII(Bg) and BamHI(Ba) cleaved $^{32}$P-labeled DNA from Vero cells infected with HSV-1 (Justin).

The present invention relates to a substantially pure culture of a human herpesvirus, having the identifying characteristics of ATCC accession number CRL 10505, and designated human herpesvirus-7 (HHV-7), according to the rules of the Herpesvirus Study Group of the International Committee for Taxonomy of viruses (Roizman, B., Carmichael, L. E., Deinhardt, F., de-The, G., Nahmias, A. J., Plowright, W., Rapp, F., Sheldrick, P., Takahashi, M., Wolf, K., (1981). Intervirol. 16. 201–217). The HHV-7 virus produces a cytopathic effect in peripheral blood mononuclear cells. The virus may be activated by conditions leading to T cell activation. The infected cells must be activated in order for the virus to be recovered.

The closest known viral strain to HHV-7 is HHV-6. However, HHV-7 differs from the previously characterized T lymphotropic HHV-6 by several criteria. First, while the DNAs of the Z29 and U1102 strains of HHV-6 exhibited only limited restriction enzyme polymorphism, the digestion patterns of HHV-7 DNA were very distinct. Second, large DNA fragments of HHV-6 DNA did not hybridize to HHV-7 DNA or exhibited only partial homology. By comparison, the genomes of HSV-1 and HSV-2 (which are classified as different herpesviruses) are colinear and exhibit cross hybridization with all large probes. Also, as a further example of relatedness between different herpesviruses, HHV-6 and HCMV appear to be related by recent sequence analyses of 21 kb of HHV-6 DNA (Lawrence, G. L., M. Chee, M., Craxton, M. A., Gompels, R. W., Honess, R. W., and Barrell, B. G., 1990, J. Viral., 64: 287–288). HHV-7 also cross hybridizes with some HCMV sequences. Thus, there are sequences which appear to be conserved amongst the cytomegalovirus-like viruses, including HHV-6 and HHV-7. Thirdly, preliminary results have revealed that HHV-7 differs from HHV-6 with respect to antigenic properties of its proteins. Such differentiation is employed in diagnostic tests of the present invention.

The present invention further includes a method of preparing a substantially pure preparation of HHV-7, preferably comprising isolating CD4+ T cells from an infected individual, then activating the T cells, and then isolating the virus from the T cells.

The present invention also includes a method of preparing a substantially pure preparation of HHV-7, preferably comprising isolating peripheral blood lymphocyte cells from an infected individual, activating the lymphocyte cells, contacting the activated lymphocyte cells with uninfected preactivated peripheral blood lymphocyte cells, at least one time, and isolating the virus from the infected lymphocyte cells. In addition, the step of contacting the activated lymphocyte cells with uninfected preactivated peripheral blood cells may be repeated, and DNA may be extracted for identification of the virus using DNA analyses well known in the art.

HHV-7 is prepared from peripheral blood mononuclear cells from an infected individual or from an individual where the virus is latent. Mononuclear cells are prepared from heparinized blood. Virus replication requires that the cells be activated first before a productive infection can take place. The cells are then activated and the virus is recovered therefrom using methods well known to those skilled in the art.

The present invention further relates to a recombinant DNA construct and to a host cell transformed therewith. Using standard methodology well known in the art, a recombinant DNA construct comprising a vector and a DNA fragment of at least 15 nucleotides of the DNA of the human herpesvirus-7 can be constructed without undue experimentation. Also, using standard methodology well known in the art, a recombinant DNA construct comprising a vector, a copy DNA of viral mRNA, and a promoter driving expression of the gene can be constructed without undue experimentation. The DNA fragment can be isolated from human mononuclear cells or it can take the form of a cDNA clone produced using methods well known to those skilled in the art. The host cell can be prokaryotic (such as bacterial), lower eukaryotic (such as fungal, including yeast) or higher eukaryotic (such as mammalian).

The present invention further includes a recombinant construct comprising a vector, a copy DNA of viral mRNA and a promoter driving expression of the gene, where the construct produces a clone from which a substantially pure protein is expressed. Furthermore, the present invention relates to a bioassay for the detection of the copy DNA, wherein the copy DNA is detected with antibodies specific for the copy DNA. Specifically, a bioassay can be constructed by coating on a surface (i.e. a solid support) for example, a gel, a slide, a microtitration plate or a membrane or column material such as sepharose beads, all or at least 15 nucleotides of the copy DNA and contacting it with a biological sample, such as serum, from an individual suspected of being infected with HHV-7. The presence of a resulting complex formed between the surface and antibodies specific therefor in the serum can be detected by any of the known methods common in the art, such as by direct or indirect (sandwiched) detection of human immunoglobulin, (e.g. IgG, IgM, IgA) and the detection of the complex by common methods such as by fluorescence, spectroscopy, colorimetry or bioluminescence.

The present invention relates to substantially pure forms of antibodies specific for HHV-7 and to a substanatially pure form of a protein expressed from the copy DNA of the viral mRNA of HHV-7, within a host cell transformed therewith. The present invention also includes a substantially pure form of a protein encoded in the genome of HHV-7 of the present invention and a substantially pure form of antibodies specific to the protein. One skilled in the art using standard methodology can raise monoclonal antibodies and polyclonal antibodies to the virus or the protein (or a unique portion of the protein).

The present invention includes a vaccine for use in humans against human herpesvirus-7. In one embodiment of this aspect of this invention, as is customary for vaccines, a non-infectious antigenic portion of HHV-7 can be delivered to a human in a pharmacologically acceptable vehicle. Vaccines of the present invention can include effective amounts of immunological adjuvants known to enhance an immune response. The non-infectious antigenic portion of HHV-7 is in the vaccine in an amount sufficient to induce an immune response against the antigenic portion and thus to protect against human herpesvirus-7 infection. Protective antibodies are usually best elicited by a series of 2–3 doses given about 2 to 3 weeks apart. The series can be repeated when the concentration of circulating antibodies concentration in the patient drops.

A further aspect of the present invention further includes a bioassay for the detection of a HHV-7 DNA sequence. This can be used for diagnosis of an HHV-7 infection, in particular for early diagnosis. Preferably, the assay comprises the steps of amplifying all or a portion of a DNA segment of HHV-7 by preforming a polymerase chain reaction (PCR) assay (U.S. Pat. Nos.

4,683,202 and 4,683,195) on a biological sample (such as, serum or tissue), the contents of which are incorporated herein by reference, from a patient and detecting the presence or absence of the amplified DNA segment. The DNA can be detected by, for example, running the amplified sample out on a gel and screening the gel with a probe or an antibody specific for HHV-7. The amplified segment may also be detected with antibodies specific for HHV-7.

The present invention also includes a method of detecting HHV-7 DNA in biological samples comprising contacting the sample with a nucleic acid probe under conditions such that a hybrid complex between the probe and complementary DNA within the sample is formed and then detecting the presence or absence of the hybridized probe. ClaI and HindIII DNA clones specific for HHV-7 DNA have been identified. These clones do not react with excess HHV-6 DNA or with mock infected cellular DNA. Further, the nucleic acid probe may comprise a sequence that is longer than 15 bases. DNA from test tissues or peripheral blood cells can be tested for the presence of HHV-7 DNA sequences using these clones as probes. The HHV-7 DNA may be amplified using primers specific for HHV-7. Furthermore, the presence of HHV-7 DNA sequences can be detected in tissues by in situ hybridizations, using techniques well known in the art, and employing HHV-7 DNA probes. HHV-7 PCR primers can be used to amplify HHV-7 sequences in the test tissues. In addition, virus isolates obtained from test tissues can be recognized as HHV-7 by PCR analyses and blot hybridizations using the HHV-7 specific probes.

The present invention includes bioassays for use in human medicine. For diagnosis of HHV-7 infections, the presence of antibodies to HHV-7 and/or the proteins its genome encodes in mammalian serum is determined. Many types of tests, as one skilled in the art will recognize, can be used for detection. Such tests include, but are not limited to, IFA, immunoblots, RIA, RIST, ELISA, agglutination and hemagglutination. The diagnostic assays can be performed using standard protocols.

Specifically, a bioassay of the present invention can be constructed by coating on a surface (i.e. a solid support) for example, a gel, a slide, a microtitration plate or a membrane or column material such as sepharose beads, all or a unique portion of a protein encoded in the DNA genome of HHV-7 and contacting it with a biological sample, such as serum, from a patient suspected of being infected with HHV-7. The presence of a resulting complex formed between the surface and antibodies specific therefor in the serum can be detected by any of the known methods common in the art, such as by direct or indirect (sandwiched) detection of human immunoglobulin, (e.g. IgG, IgM, IgA) and the detection of the complex by common methods such as by fluorescence, spectroscopy, colorimetry or bioluminescence.

In another bioassay of the present invention, HHV-7 infected cells are fixed on a surface and the surface is contacted with serum from a patient suspected of being infected with HHV-7. The presence or absence of the protein-antibody complex is then detected using methods well known in the art. Specifically, the complex may be detected by biotinylated antibodies, and these antibodies may be detected by streptavidin.

Further, the protein-antibody complex may be detected with fluorescein conjugated anti-human immunoglobulin G. For example, an indirect immunofluorescence (IF) test specific for HHV-7 has been developed. The test employs slides carrying acetone fixed or acetone:methanol fixed infected cells. Following incubation with different dilutions of the test sera the slides are reacted with fluorescein conjugated anti-human IgG. The test can be used to determine the presence of HHV-7 antibodies in human sera, and to identify HHV-7 isolates obtained from test tissues. It has recently shown that the IF test is specific for HHV-7. For example the test can distinguish seroconversion to HHV-6 and HHV-7.

In another bioassay HHV-7 purified virions are prepared by purification of virus by velocity sedimentation which yields fractionating by size and shape, such as in sucrose or glycerol gradients, or through equilibrium density sedimentation, which yields fractionating by density, such as through Dextran gradients or CsCl gradients, or through high pressure liquid chromatography techniques, or by panning techniques such as on a surface containing specific antibodies which allows specific attachment and purification of the virions or by passing through columns which contain specific antibodies to the virions. The purified virions are fixed on solid support such as the surface of microtiter plate, or on membrane, or in columns, for example, by linking to Sepharose or other kinds of beaded material. The virions on the solid surface are then contacted with serum from a patient suspected of being infected with HHV-7. The formation of the antibody complex is detected by known methods common in the art, such as by direct or indirect (sandwiched) detection of human immunoglobulin, (e.g. IgG, IgM, IgA) and the detection of the complex by common methods such as by fluorescence, spectroscopy, colorimetry or bioilluminescence.

Western blot tests employing proteins from HHV-7 infected cells have been developed, allowing the detection of antibodies to specific HHV-7 proteins. In these tests Western blots are prepared by electrotransfer of infected cell proteins. The blots are incubated with test serum and then with biotinylated anti-human IgG. Reaction is detected with streptavidin alkaline phosphatase. Using this test the inventor has been able to detect HHV-7 specific antibodies in human sera. Several tested sera contained antibodies directed against a major antigen (83 kDa), and also against minor proteins (74 and 67 kDa).

In another bioassay of the present invention, the presence or absence of HHV-7 in a serum sample is detected. Antibodies specific for HHV-7 can be coated on a solid surface such as a plastic and contacted with the serum sample. After washing, the presence or absence of the virus from the serum bound to the fixed antibodies is detected such as by addition of a labeled (e.g. fluorescent) antibody specific for the virus.

In another bioassay of the present invention, the presence or absence of a protein of the virus in a serum sample is detected. Antibodies specific for a protein can be coated on a solid surface such as a plastic and contacted with the serum sample. After washing, the presence or absence of the protein of the virus from the serum bound to the fixed antibodies is detected such as by addition of a labeled (e.g. fluorescently labeled) antibody specific for the protein.

EXAMPLES

The following non-limiting Examples are provided to describe the invention in greater detail.

Human herpesvirus-7 was deposited on Jul. 13, 1990, at the American Type Culture Collection, 12301 Parklawn Drive, Rockville, Md. 20852. The deposit number is CRL 10505, and comprises blood cells infected with the RK strain of Human Herpesvirus-7. Deposit is for the purpose of enabling disclosure only, and is not intended to limit the concept of the present invention to the particular biological material deposited.

Isolation of HHV-7 Strains from Peripheral Blood Lymphocytes.

From a healthy individual (RK), two variant isolates of strain RK (RK isolates 1 and 2) were made from purified CD4+ T cells purified from peripheral blood of a 24 year old healthy individual using techniques well known in the art. Further studies have shown that virus isolation could be made from non-fractionated PBL and this procedure is described here. The strains HHV-7(3), HHV-7(4) and HHV-7(5) were isolated from the unfractionated peripheral blood mononuclear cells. Specifically, lymphocytes were purified from fresh heparinized peripheral blood (PBL) by centrifugation in lymphocyte separation medium (Organon Technika). The cells were activated by exposure to medium containing 10 ug/ml phytohemagglutin (PHA) for several days after which the activated cells were mixed with uninfected preactivated PBL. The preactivation of the recipient cells was by incubation of PBL (freshly isolated or frozen) for 2-3 days in RPMI medium containing 10% fetal calf serum and 10 ug/ml PHA. The process of mixing the culture with another batch of PBL was repeated "blindly", at which time the cultures were tested by immunofluorescence assay for the potential presence of the virus, using serum positive for HHV-7. If positive, the culture was suspected of harboring virus. The putative virus was further propagated in preactivated PBL to amplify the virus, at which point the DNA was extracted and identified as HHV-7 using DNA analyses. Several points are noteworthy concerning this process.

All the initial isolates of HHV-7 (the strains RK, 3, 4, and 5) appear to have been activated from latency by exposing the cells to conditions leading to T cell activation. Thus, no virus could be recovered from the freshly isolated quiescent cells unless the cells were activated, nor was it possible to transmit the virus by further passaging in PBL unless the recipient PBL were preactivated.

Figure 7:
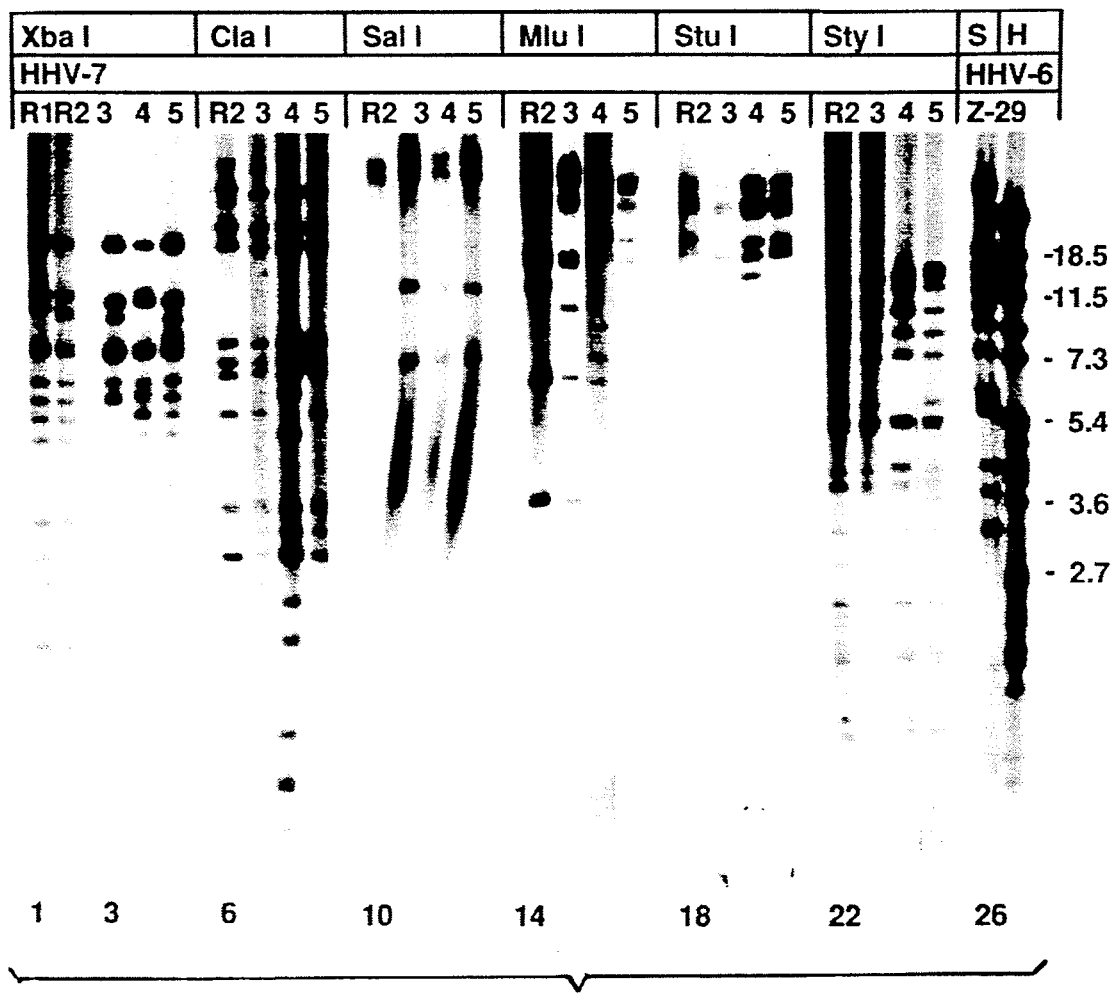
FIG. 7 shows restriction enzyme analyses of $^{32}$P-labelled DNAs from four independently isolated HHV-7 strains and from HHV-6.

FIG. 7 shows that the viruses RK, 3, 4, and 5 all possess similar restriction enzyme patterns characteristic for HHV-7, but they also showed minor polymorphism. The viruses were independently isolated from peripheral blood lymphocytes (PBL) of four individuals. The HHV-7 strain RK was isolated from purified CD4+ cells and the strains HHV-7 (3), HHV-7 (4), and HHV-7 (5) were prepared from total PBL. Lanes 1-25 contain the HHV-7 DNAs cleaved by the enzymes Xbal, Clal, Sall, Mlul, Stul, and Sty 1. Lanes 26 and 27 contains HHV-6 DNA digested with Sall (s) and Hindlll (H). The figure shows that the DNAs of HHV-7 strains RK, 3, 4, and 5 all possess similar restriction enzyme patterns characteristic of HHV-7. Furthermore, comparison of the Sall patterns of HHV-7 (lanes 10-13) and HHV-6 (lane 26) shows that the genes of HHV-7 and HHV-6 are very different. The limited restriction enzyme polymorphism is a well known phenomenon with other herpesvirses (e.g. for herpes simplex virus). This allowed us to conclude that the isolates RK, 3, 4, and 5 described here were indeed separate strains which arose by the rescuing of latent virus from different individuals.

Virus was isolated from 3 PBL cultures (yielding isolates 3, 4 and 5) out of approximately 30 PBL cultures which were tested by repeated "blind" passages of the type described here. In each case virus propagation was attempted using recipient PBL found to be clean of latent virus, by repeated continued "blind" passaging. Specifically, to derive these "clean" PBL after purification of the mononuclear cells from peripheral blood, the cells were frozen in small aliquots which could then be unfrozen when desired and tested. Cultures which did not give rise to any virus after 6-7 "blind" passaging were judged to be "clean" and could be used for additional virus isolation attempts from other PBL and from patients potentially infected with the virus.

Repeated Isolation of HHV-7. Strain (5)

Aliquots of the PBL suspected of giving rise to strain 5 were frozen prior to their activation by PHA and virus isolation from the frozen cells was attempted two additional times. In both cases the same HHV-7 strain was successfully rescued as shown by identical restriction enzyme patterns of the resultant isolates. (FIG. 7)

Further Virus Propagation

Briefly, PBL were precultured for 3 days in RPMI-10% medium (RPMI 1640 medium+50 $\mu$g/ml gentamicin+10% heat inactivated fetal calf serum) containing 10 $\mu$g/ml phytohemagglutinin (PHA, Difco Laboratories). Infection was done in RPMI-10% medium.

Electron Microscopy Analyses

Cell pellets were treated sequentially with glutaraldehyde and osmium tetroxide (1% each for 30 minutes in 0.1M cacodylate buffer, pH 7.2), stained with 1% uranyl acetate and dehydrated in graded ethanol solutions (30% to 100%). After propylene oxide treatment the samples were embedded in PolyBed 812 (Polysciences) and sectioned with an ultramicrotome. Sections of 70-80 nm thickness were examined in the Philips-300 electron microscope.

Analysis of thin sections prepared from cells infected with RK virus revealed typical herpesvirus virions (Roizman, B. (1982) in The herpesviruses. Vol. 1. ed. Roizman, B. (Plenum, New York), pp. 1-23), 170 nm in diameter and containing an electron dense cylindrical core, a capsid, a tegument and an envelope (FIG. 1e and 1f). The virions contained a very distinct tegument layer between the capsid and the envelope, similar to that observed in HHV-6 virions.

Preparation of Infected Cell DNA

Unlabeled infected cells were harvested at the peak of CPE. $^{32}$P-labeling of infected cell DNA was as previously described (Di Luca, D., Katsafanas, G., Schirmer, E., Balachanran, N., and Frenkel, N. (1990) Virol. 175:199-210 (1990)).

DNA Probes pHeHE was cloned by Drs. A. Marchini and E. Kieff (Harvard University). It contains the EBNA-1 and Ori-P DNA sequences of Epstein Barr virus. The cloned EcoK fragment of varicella zoster virus (VZV) DNA, as well as purified intact VZV DNA, were obtained from Dr. W. T. Ruyechan (Uniformed Services University of the Health Sciences). pON203, obtained from Dr. E. S. Mocarski (Stanford University), contains human cytomegalovirus (HCMV) DNA sequences. HCMV infected cell DNA was prepared from human foreskin fibroblasts infected with HCMV (Towne). pHD9, pSMD2, and pSAD2a are clones of HHV-6 (U1102) obtained from Dr. R. W. Honess (National Institute of Medical Research, London). pNF182 contains the BglII N fragment of herpes simplex virus 2 (HSV-2) strain 333 DNA pNF1021, pNF1022, pNF1019, pNF1023 contain SalI fragments of HHV-6 (U1102) DNA, whereas pNF1001, pNF1006, pNF1010 and pNF1013 contain SalI or HindIII fragments of HHV-6 (Z29) DNA. The clones p7F2001, p7F2002, and p7F2004 contained HHV-7 ClaI fragments of size 8.5 kb, 4.5 kb and 1.3 kb, respectively.

Southern Blot Hybridizations

The DNA was digested with restriction enzymes and electrophoresed in 0.7% agarose gels. Following ethidium bromide staining, the DNA was blotted onto Nytran (Schleicher and Schuell). The membranes were prehybridized overnight at 67° C. in hybridization buffer containing 6×SSC, 2×Denhardt's solution (Denhardt, D. T. (1966). Biochem. Biophys. Res. Commun. 23, 641–646), 0.5% SDS and 150 mg/ml denatured salmon sperm DNA. The probe DNA was labeled with $^{32}$P-dCTP (NEN) using multiprime DNA labeling system (Amersham). Hybridization was at 67° C. in hybridization buffer (50 ml/cm$^2$) containing 300,000 CPM/ml. The blots were washed at 67° C. in 6×SSC, then 1×SSC and 0.5×SSC prior to autoradiography.

Restriction Enzyme Analyses of Viral DNA

Because of the T cell origin of the RK virus it was originally suspected that the new virus was a strain of HHV-6. Cells were infected with RK isolates 1 and 2, and with the HHV-6 strains Z29 (Lopez, C., Pellett, P., Stewart, J., Goldsmith, C., Sanderlin, K., Black, J., Warfield, D., Feorino, P. (1988) J Infect Dis 157, 1271-73) and U1102 (Downing, R. G., Sewankambo, N., Serwadda, D., Honess, R., Crawford, D., Jarrett, R., Griffin, B. E. (1987) Lancet ii, 390). Host DNA replication is shut-off after HHV-6 infection (Di Luca, D., Katsafanas, G., Schirmer, E., Balachanran, N., and Frenkel, N. (1990) Virol. 175:199–210 (1990)). Therefore a significant fraction of $^{32}$P-orthophosphate can be preferentially incorporated into viral DNA. $^{32}$P-labeled HHV-6 and HHV-7 infected cell DNAs were analyzed using 21 restriction enzymes. Representative patterns are shown in FIG. 2. The results can be summarized as follows: (i) The restriction enzyme patterns of the HHV-6 strains Z29 and U1102 were not identical but were generally similar and many of the fragments comigrated in the gel. It should be noted that variations in a single restriction enzyme site is expected to result in non-identity of three bands when the two patterns are compared. (ii) In contrast, the cleavage patterns of the RK isolates differed significantly from Z29 and U1102 patterns. In fact, the majority of the fragments did not comigrate. Some enzymes produced a different distribution of fragments: large fragments from the RK virus DNA compared to relatively small fragments from the Z29 and U1102 DNAs (e.g., SalI, PstI, Sac I and MluI, FIG. 2) and vice versa (HindIII, FIG. 2). (iii) The patterns exhibited by isolates 1 and 2 of the RK virus were very similar and a majority of the fragments comigrated in the gel. However, in some of the patterns some subtle differences were noted (demarcated with arrows, FIG. 2). The difference reflected a variability in size of one small region of the genome.

Homology to pHD9 Clone of HHV-6 (U1102)

Figure 3:
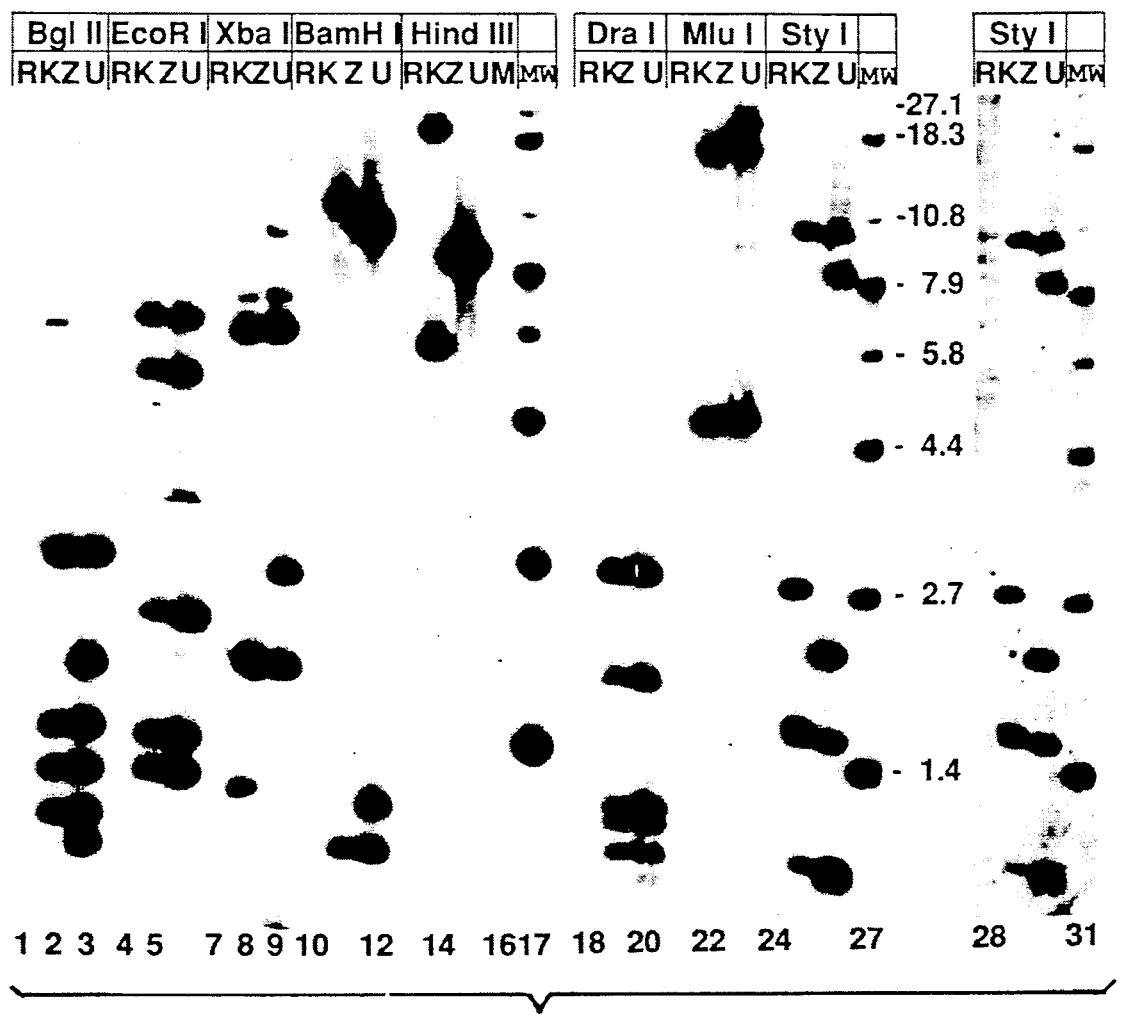
FIG. 3 shows lack of hybridization of pHD9 which contained a large insert (9 kb) of HHV-6 DNA to HHV-7 infected cell DNAs.

The marked differences between the restriction enzyme patterns of RK virus DNA and those of the two HHV-6 strains raised the question whether these viruses share DNA sequences. DNAs from cells infected with the RK virus, and the HHV-6 strains Z29 and U1102 were cleaved with restriction enzymes, blotted and hybridized with a number of probes derived from the two HHV-6 strains. FIG. 3 shows lack of hybridization of pHD9 which contained a large insert (9 kb) of HHV-6 DNA to HHV-7 infected cell DNAs. Lanes 1–27:hybridization with $^{32}$P- labeled pHD9 probe derived by Honess and coworkers from HHV-6 (U1102). The blot contained DNAs from mock infected cells (M) or from cells infected with HHV-6 strains Z29 (Z) and U1102 (U), or RK virus (RK) cleaved with the enzymes shown. Only the lanes containing the HHV-6 infected cell DNAs are seen to be hybridize. In contrast, the HHV-7 infected cell DNA does not hybridize this large HHV-6 probe. To ascertain that the lack of hybridization indeed reflected lack of sequence homology, the blot was then hybridized (without stripping the pHD9 probe) with $^{32}$P-labeled RK virus DNA labeled in vivo. Lanes 28–31 show the rehybridized blot portion shown in lanes 24–27. The HHV-7 DNA fragments are now seen to hybridize with the homologous HHV-7 probe. This control shows that the blot contained HHV-7 DNA sequences which could hybridize with probes. The lack of hybridization of the pHD9 probe therefore proves that the HHV-7 DNA did not contain sequences homologous to this large (9 kb) pHD9 probe of HHV-6. Lanes 17, 27 and 31 include mw markers which hybridize with the plasmid portion of the pHD9 probe.

In the first hybridization (FIG. 3, lanes 1–27), DNA from the RK virus and HHV-6 strains Z29 and U1102 was cleaved with 11 enzymes and hybridized with the probe pHD9 which contains a 9 kb HindIII insert of U1102 DNA. The probe hybridized strongly to both U1102 and Z29 DNAs yielding very similar patterns. In contrast, no hybridization was noted in the RK lanes. Three lines of evidence suggest that the lack of hybridization represented lack of homology between RK DNA and the probe sequences rather than the presence of insufficient amounts of RK virus DNA on the blot. First, the ethidium bromide staining of the gels prior to blotting revealed the presence of large amounts of infected cell DNA. Second, the same quantities of DNA were loaded onto sister blots which gave positive signals with other probes (see below). Thirdly, following autoradiographic exposure, the blot shown in FIG. 3 was hybridized with RK virus infected cell DNA, labeled in vivo with $^{32}$P. The specific activity of the in vitro labeled pHD9 probe was more than 1000-fold higher than that of the in vivo labeled infected cell DNA. Nonetheless, the in vivo labeled DNA hybridized to the homologous RK DNA on the blot, yielding all of the expected bands in the pattern (FIG. 3. lanes 28–31). No additional hybridization was noted with the heterologous HHV-6 strains Z29 and U1102 DNAs and the only visible bands remained the previously hybridized pHD9 bands. This result confirms the conclusion that sufficient RK DNA was available on the blot. Therefore, the lack of pHD9 hybridization reflected the lack of homology.

Hybridizations with other U1102 and Z29 Probes

Figure 4:
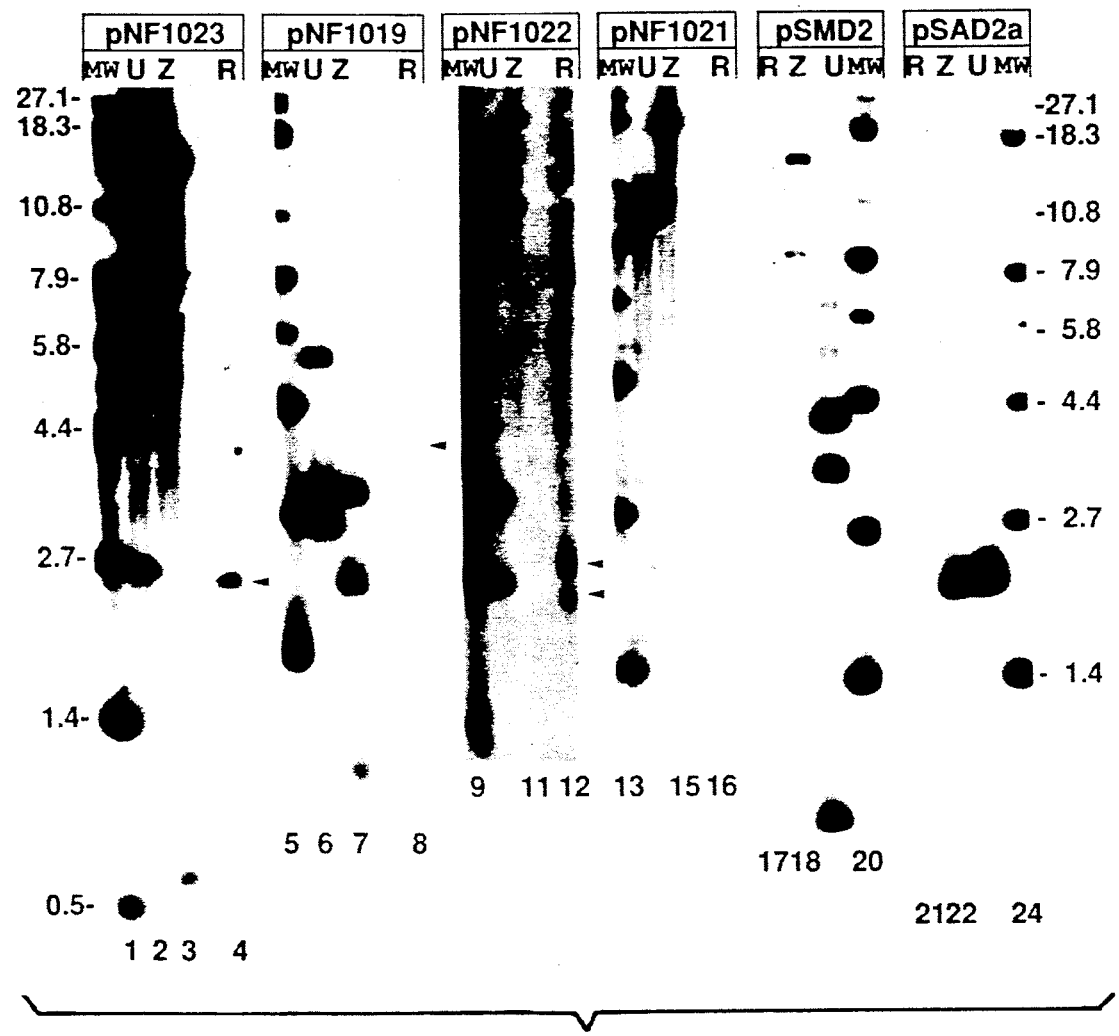
FIG. 4 shows hybridization of HHV-6 (U1102) probes to HHV-6 (Z29 and U1102) and to RK virus DNAs. HindIII digested DNA was blotted and hybridized with the $^{32}$P-labeled probes shown. MW refers to size markers which hybridize with the plasmid portions of the probes. The arrows for the hybridized probes pNF 1023, pNF 1019 and pNF 1022 point to the hybridizing HHV-7 (RK) bands.
Figure 5:
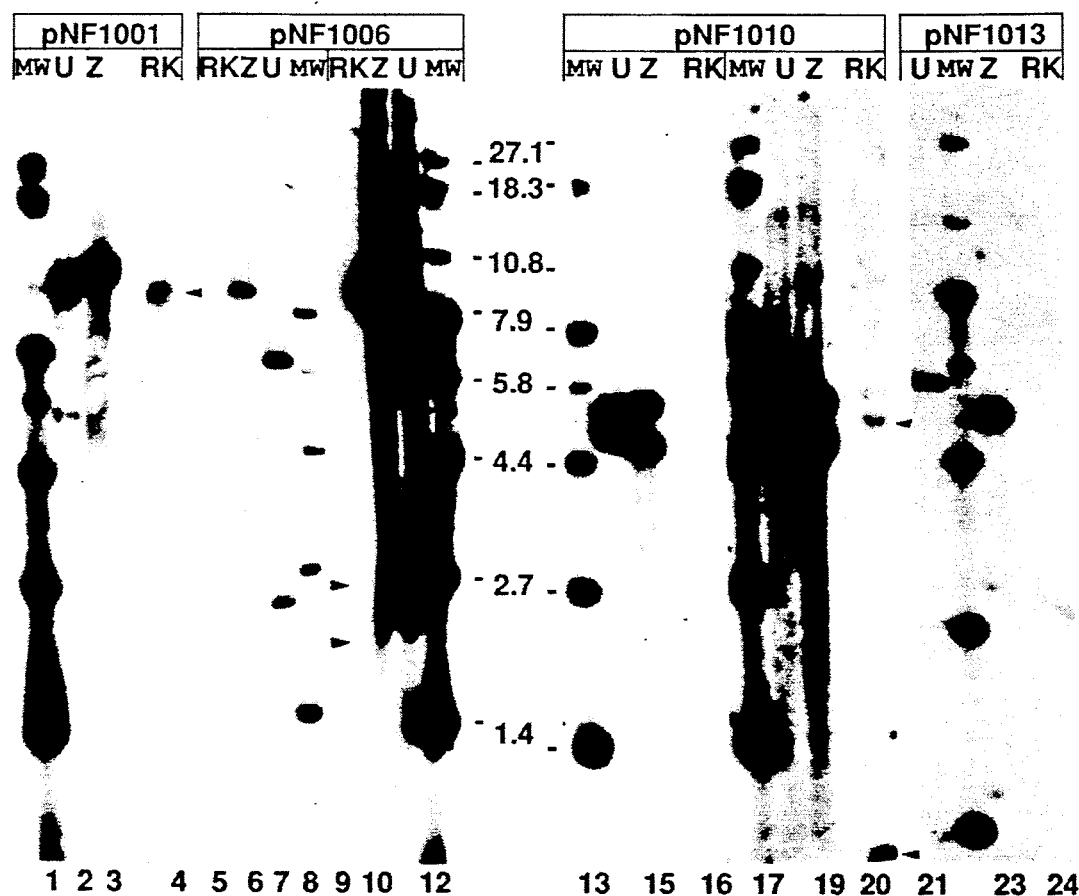
FIG. 5 shows hybridizations using HHV-6 (Z29) probes.

Additional analyses with six U1102 probes and four Z29 probes are shown in FIGS. 4 and 5. The results can be summarized as follows: (i) The U1102 probes pNF1021, pSMD2 and pSAD2a, containing inserts of 6 kb, 2.1 kb and 2.3 kb, respectively, did not hybridize with RK virus DNA (FIG. 4, lanes 14-24). The remaining 3 probes, pNF1023, pNF1019, and pNF1022 containing inserts of 11.5 kb, 5.8 kb and 3.9 kb, respectively, yielded weak hybridization bands (FIG. 4, arrows lanes 1-13). Note that hybridization is to small fragments, revealing only partial homology with the probe. No hybridization was detected between HHV-7 DNA and HHV-6 probes pNF 1021, pSMD2 and pSAD2a. In each case, the aggregate molecular weight of the hybridized fragments was lower than the complexity of the U1102 fragment used as probe. For example, the 11.5 kb insert in pNF1023 hybridized only to a 2.3 kb RK virus DNA fragment (FIG. 4. lane 4). It is estimated that a maximum of 11.2 kb hybridized with the 40.5 kb U1102 test probes.

FIG. 5 shows hybridizations using HHV-6 (Z29) probes. Blots containing HindIII digests of DNAs from cells infected with HHV-6 (Z29 and U1102), and HHV-7 (RK) were hybridized with the HHV-6 (Z29) probes shown. Lanes 9-12 show long exposure of lanes 5-8, and lanes 17-20 show long exposure of lanes 13-16. The HHV-7 (RK) hybridized bands are marked with arrows. Again, note the low intensity of hybridized HHV-7 DNA, showing only partial homology. The four Z29 probes used were SalI or HindIII clones containing relatively large inserts of sizes 5, 8.8, 9 and 12 kb. Of these clones, pNF1013 (5 kb insert) did not hybridize to RK virus DNA (FIG. 5, lane 24). The larger clones revealed weak hybridization apparent only after lengthy autoradiography (FIG. 5 lanes 4, 9 and 20). Once again, the aggregate sum of molecular weight of the hybridizing fragments was lower than the size of the Z29 test insert. The probes totaling 34.8 kb hybridized to RK DNA fragments totaling 19.6 kb. The lower intensity of hybridizing bands might reflect incomplete sequence homology resulting in less stable hybrids. Thus, these estimates most likely represent maximal values of homology. Once again, the fact that some hybridization was noted serves as a control for the blotting efficiency.

Hybridization Analyses Using Probes from other Herpesviruses

Figure 6:
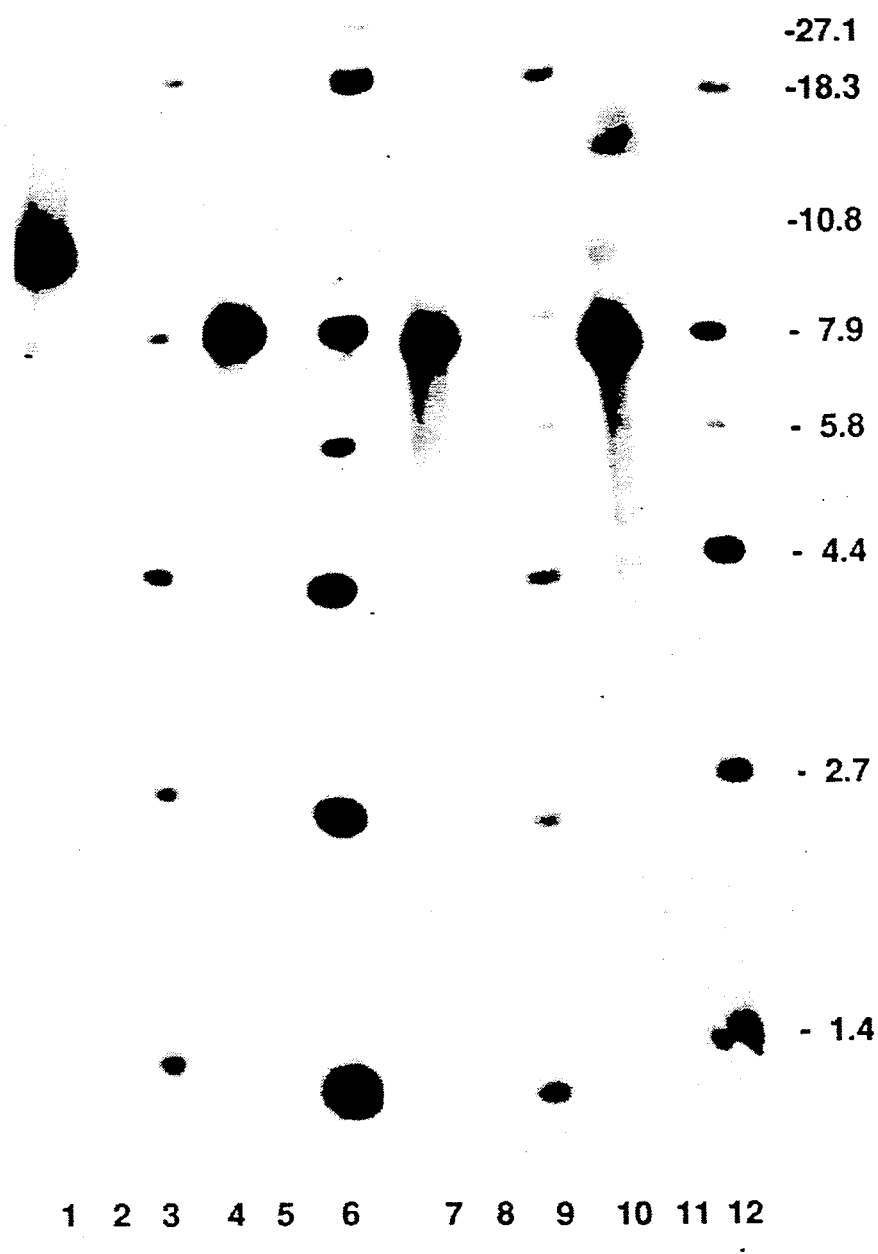
FIG. 6 shows hybridization tests using probes derived from other herpesviruses. The blot contained DNA from HHV-7 (RK) infected cells (lanes 2,5,8, and 11), pHeHE DNA (lane 1,BamHI digested), HCMV (Towne) infected cell DNA (lane 4,BamHI digested), VZV DNA (lane 7, EcoRI digested), and DNA from HSV-2 infected cells (lane 10, BglII digested).

As indicated by FIG. 6, additional tests were done using probes derived from other herpesviruses, including EBV, HCMV, VZV and HSV-2. The probes contained 2 kb EBV DNA sequences (pHeHE), 7.6 kb HCMV DNA (pON203), 7.3 kb VZV DNA (EcoK) and 7.6 kb HSV-2 DNA sequences(pNF 182). No hybridization is detected between these large probes and HHV-7 DNA. No hybridization was noted with these probes. It is concluded that RK virus is not identical these previously characterized human herpesviruses. These hybridizations however do not exclude the possibility that RK virus DNA contains more highly conserved sequences of herpesvirus genomes.

For virus isolation and growth, test specimens are incubated with carrier cells such as T cell lines. Because not all naturally occurring isolates can be propagated in cell lines virus isolation and propagation must also be done using cord or peripheral blood lymphocytes. The indicator cells are tested (by PCR analysis) for the presence of live or latent virus prior to their use as indicator carrier cells. Tested cells can be frozen and used when needed. For efficient virus replication, the indicator cells are first activated, e.g., by culturing the cells in the presence of 5 $\mu$g/ml phytohemagglutinin (PHA) and low amount of interleukin-2. Virus can then be identified as HHV-7 by the methods described above.

The Derivation of Clones from HHV-7 DNA

Figure 8:
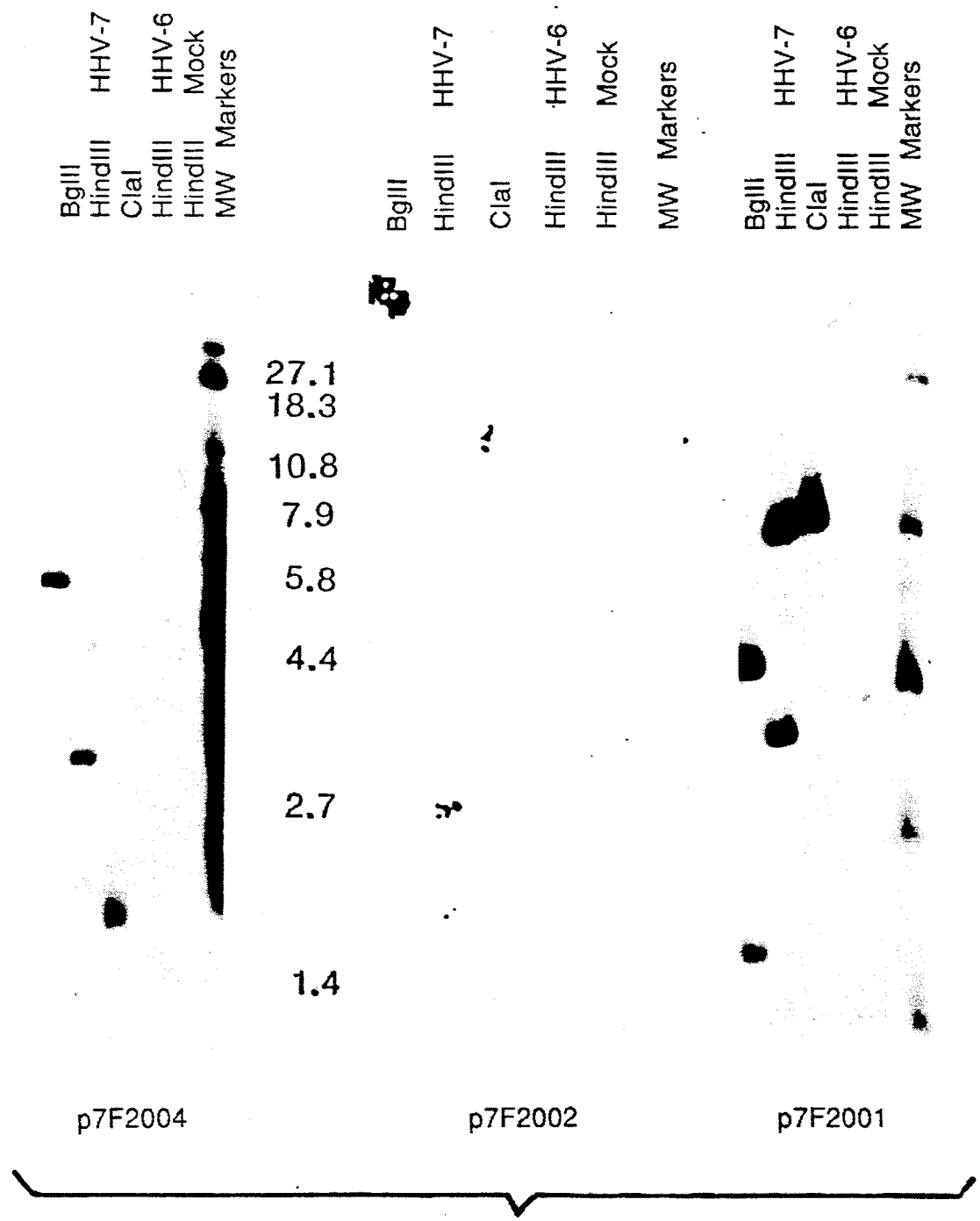
FIG. 8 shows hybridization of $^{32}$P-labelled clones of HHV-7 DNA to blots containing BglII, HinIII and ClaI digested DNAs from HHV-7 infected cells and to HindIII digested DNAs from HHV-6 infected cells and mock infected cells.

Viral DNA extracted from HHV-7 infected cells was digested with ClaI or HindIII enzymes and then cloned using the plasmid pKC7 as the vector, using standard cloning procedures. The resultant clones were tested for their HHV-7 specificity by blot hybridizations. Such blot hybridizations using as probes the clones p7F2001, p7F2002, and p7G2004 are shown in FIG. 8. The blot contained ClaI, HindIII, and BgIII digested DNAs extracted from HHV-7 infected cells, as well as HindII digested DNA from mock infected cell DNA, and form cells infected with HHV-6 strain Z29. Only the HHV-7 lanes show hybridizations. Thus, the clones are specific for HHV-7 DNA. the clones contain the following inserts:

p7F 2001 contains a 8.5 kb ClaI fragment
p7F 2002 contains a 4.5 kb ClaI fragment
p7F 2004 contains a 1.3 kb ClaI fragment These probes hybridized only to the HHV-7 infected cell DNA.

Restriction Enzyme Analyses

Restriction enzyme analyses was performed using $^{32}$P-labelled DNAs from four independently isolated HHV-7 strains and from HHV-6 (FIG. 7). The DNAs of HHV-7 strains RK 3, 4 and 5 all possess similar restriction enzyme patterns characteristic for HHV-7. Also, comparison of SalI patterns of HHV-7 (lanes 10-13) and HHV-6 (lae 26) shows that the genomes of HHV-7 and HHV-6 are different.

Hybridization of $^{32}$P-labelled Clones of HHV-7 DNA

Hybridization of $^{32}$P-labelled clones of HHV-7 DNA was done to blots containing Bgl11, Hin111 and ClaI digested DNAs from HHV-7 infected cells and to HindIII digested DNAs from HHV-6 infected cells and mock infected cells (FIG. 8). Only the HHV-7 lanes show hybridization, and thus, the clones are specific for HHV-7 DNA.

Western Blot Analyses of Proteins from HHV-7 Infected Cells

Figure 9:
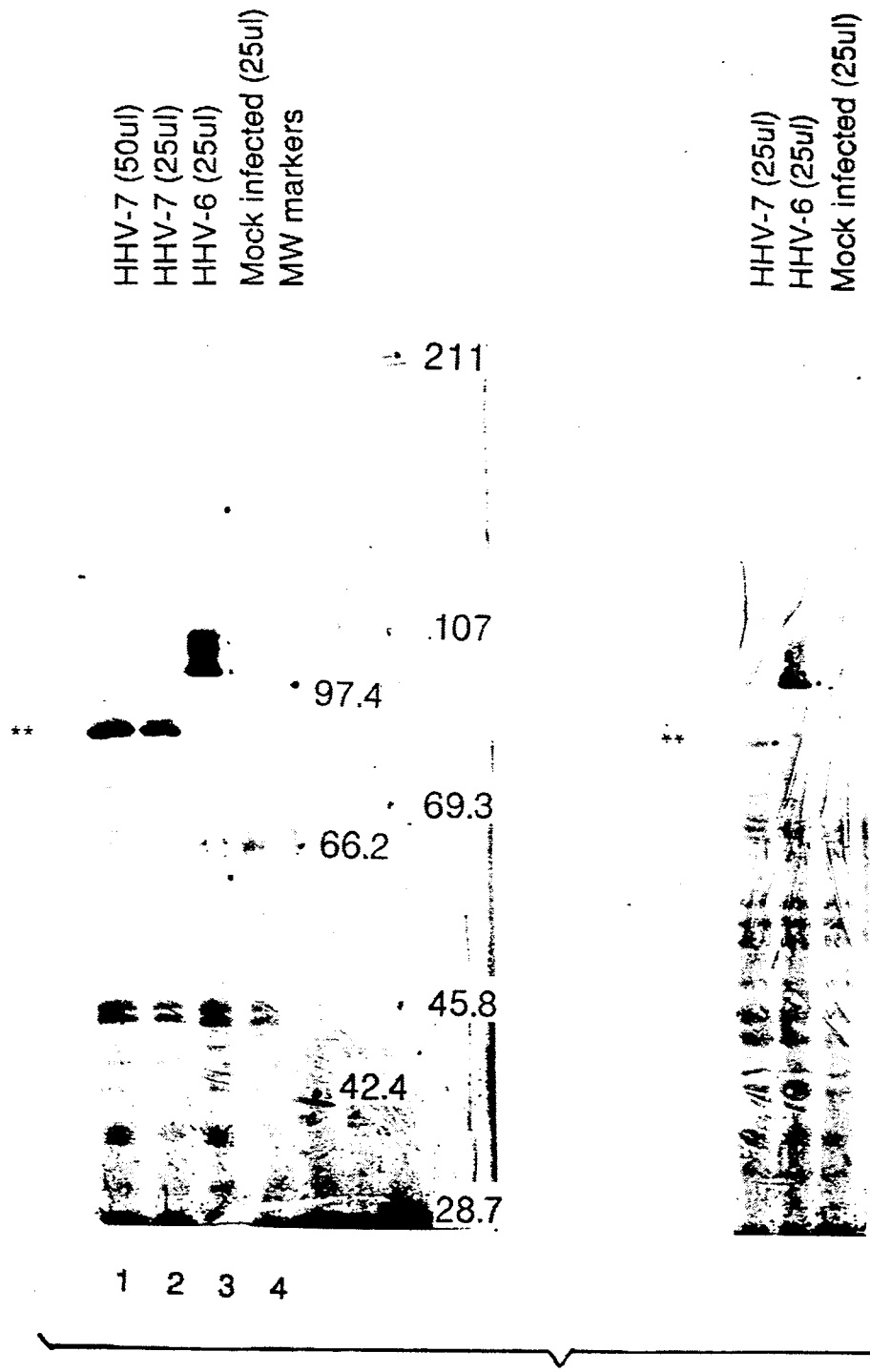
FIG. 9 shows Western blot analyses of proteins from HHV-7 infected cells. (A): PBL cultures were infected with HHV-7 or with HHV-6 or were mock infected. (B): A similar Western blot was reacted with pooled human IgG (commercially available), showing the reactivity of the ** band specific for HHV-7.

FIG. 9 shows Western blot analyses of proteins from HHV-7 infected cells. PBL cultures were infected with HHV-7 or with HHV-6 or were mock infected. The infected cell proteins were electrophoresed in a polyacrylamide gel and then electroblotted. The blots were reacted with human serum (at 1:50 dilution), then with biotinylated anti-human lgG and then with streptavldin alkaline phosphatase. Lanes 1 and 2 contain 50 ul and 25 ul respectively, of the HHV-7 infected cell lysate. Lane 3 contains 25 ul of the HHV-6 infected cell lysate, and lane 4 contains 25 ul of mock infected cell lysate. The  marks a major immunogenic protein specific for HHV-7 of estimated mw 83 kDa. The molecular weights were estimated on the basis of mw of two sets of markers which were electrophoresed in the same gel. A similar Western blot was reacted with pooled human IgG (commercially available), showing the reactivity of the  band specific for HHV-7.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention.

What is claimed is:

1. A method for the diagnosis of human herpesvirus-7 infection in a human patient, comprising the steps of:
   ii) coating a substrate surface with a human herpesvirus-7 structural antigen
   ii) contacting said surface with serum suspected of containing human herpesvirus-7 specific antibodies from said human patient and
   iii) detecting the presence or absence of a complex formed between said antigen and antibodies specific thereof, if present in said serum, wherein the presence of said complex indicates the presence of said infection.

2. The method of claim 1 wherein said complex is detected by biotinylated antibodies.

3. The method of claim 2 wherein said biotinylated antibodies are detected by streptavidin.

4. The method of claim 1 wherein said complex is detected with fluorescein conjugated anti-human immunoglobulin G.

5. The method of claim 1 wherein said substrate surface is a gel, a slide, membrane, a microtitration plate, or column material.

6. The method of claim 1, wherein said antigen is displayed on the surface of human herpesvirus-7.

7. A method for the diagnosis of human herpesvirus-7 infection in a human patient, comprising the steps of:
   i) coating a surface with antibodies a human herpesvirus-7 structural antigen;
   ii) obtaining a biological sample from said patient;
   iii) contacting said surface with said sample; and
   iv) detecting the presence or absence of a complex formed between said antibodies and virus, if present in said sample, wherein the presence of said complex indicates the presence of said infection in said patient.

8. The method of claim 7, wherein said antigen is displayed on the surface of human herpesvirus-7.

9. A method of detecting the presence of human herpesvirus-7 infection in a patient, comprising the steps of:
   obtaining a sample of serum suspected of containing herpesvirus-7 specific antibodies from said patient;
   contacting said sample of serum with a human herpesvirus-7 structural antigen; and
   determining if specific binding has occurred between said antigen and the antibodies, if contained in said serum sample,
   wherein the presence of said specific binding indicates the presence of human herpesvirus-7 infection in said patient.

10. The method of claim 9, wherein the determining step comprises a test selected from the group consisting of IFA, immunoblots, RIA, RIST, ELISA, agglutination and hemagglutination.

11. The method of claim 9, wherein said antigen comprises an immunogenic protein of human herpesvirus-7 having a molecular weight of approximately 83 kilodaltons.

12. The method of claim 9, wherein the contacting step comprises contacting said serum with proteins from human herpesvirus-7 infected cells.

13. The method of claim 12, additionally comprising electrophoresing said proteins from human herpesvirus-7 infected cells prior to the contacting step.

14. The method of claim 13, wherein the determining step comprises determining whether any antibodies in said serum component have specifically bound to protein having an apparent molecular weight of approximately 83 kilodaltons in the electrophoresis system used for the electrophoresis step.

15. The method of claim 13, wherein the electrophoresing step comprises subjecting said proteins to polyacrylamide gel electrophoresis, resulting in a gel with separated proteins, additionally comprising blotting the proteins in said gel to another material.

16. The method of claim 15, wherein the contacting step comprises a first contacting step wherein said serum is contacted with said material.

17. The method of claim 16, additionally comprising a second contacting step wherein antibodies specific for human herpesvirus-7 specific antibodies are contacted with said material, said second contacting step being performed subsequently to said first contacting step.

18. The method of claim 17, wherein the determining step comprises determining whether said antibodies specific for human herpesvirus-7 specific antibodies are specifically bound to said material.

19. The method of claim 17, wherein said antibodies specific for human herpesvirus-7 specific antibodies carry a label.

20. The method of claim 19, wherein said label comprises biotin.

21. A method of detecting the presence of human herpesvirus-7 infection in a patient, comprising the steps of:
   obtaining a biological sample from said patient;
   contacting said biological sample with an antibody specific to a human herpesvirus-7 structural antigen;
   determining if specific binding has occurred between said antibody and said antigen present in said sample,
   wherein the presence of said specific binding indicates the presence of human herpesvirus-7 infection in said patient.

22. A monoclonal antibody specific for a human herpesvirus-7 structural antigen, but not for other human herpesviruses.

23. An isolated antibody that specifically binds to a human herpesvirus-7 structural antigen, but not to any other herpesviruses.

24. An antibody according to claim 23, wherein said antibody does not specifically bind to any exposed epitope of human herpesvirus-6.

25. An antibody according to either claim 22 or claim 23, wherein said antibody is specific for an antigen displayed on the surface of human herpesvirus-7.

26. An antibody according to either claim 22 or claim 23, wherein said antigen is a protein encoded by human herpesvirus-7 DNA .

* * * * *